United States Patent

Molz et al.

[11] Patent Number: 5,933,472
[45] Date of Patent: Aug. 3, 1999

[54] SLICED LEVEL DISPLAY FOR X-RAY SYSTEMS

[75] Inventors: Claudius Molz, Buckenhof, Germany; Paolo Barzaghi, Merate, Italy; Gerhard Wurzer, Mantel, Germany

[73] Assignee: Siemens Aktiengesellschaft, Munich, Germany

[21] Appl. No.: 09/019,869

[22] Filed: Feb. 6, 1998

[30] Foreign Application Priority Data

Feb. 7, 1997 [DE] Germany .......................... 197 04 703

[51] Int. Cl.⁶ ........................................................ A61B 6/00
[52] U.S. Cl. ............................. 378/26; 378/205; 378/206
[58] Field of Search .............................. 378/26, 196, 206, 378/21, 23, 24, 25, 205

[56] References Cited

U.S. PATENT DOCUMENTS

| | | |
|---|---|---|
| 4,087,694 | 5/1978 | Hellstrom et al. .................. 250/445 |
| 5,657,368 | 8/1997 | Röckseisen . | |
| 5,689,545 | 11/1997 | Hopkins .................. 378/206 |
| 5,734,694 | 3/1998 | Khutoryansky et al. ............. 378/197 |

FOREIGN PATENT DOCUMENTS 87 14 181 U  3/1989  Germany .

Primary Examiner—David P. Porta
Assistant Examiner—Michael J. Schwartz
Attorney, Agent, or Firm—Hill & Simpson

[57] ABSTRACT

A slice level display for x-ray systems has a projector arranged next to a patient-support plate which emits light beam directed onto a patient on the support plate, projector being coupled to a drive system in order to displace an x-ray radiator and an exposure cassette, seated under the patient-support plate, oppositely around the light beam axis as a pivot point of their connecting line. The x-ray radiator and the exposure cassette are displaceable via separate drives that are coupled with a control unit having a position sensor associated therewith. The position sensor supplies height position signals of the projector to the control unit which are used to calculate control signals for operating the respective drives for displacing the x-ray radiator and the cassette. The projector and a displacement mechanism therefor and the height position sensor are detachably securable to the patient-support plate as a structural unit.

10 Claims, 2 Drawing Sheets

SLICED LEVEL DISPLAY FOR X-RAY SYSTEMS

BACKGROUND OF THE INVENTION

1. Field of the Invention

The present invention is directed to a slice level display for an x-ray system, the slice level display being of the type having a projector, disposed next to a patient-supporting plate, which emits a planar light beam directed onto the patient, with the x-ray radiator and the exposure cassette, disposed on opposite sides of the patient, being displaced in opposite directions relative to a pivot point defined by the intersection of the plane of the light beam with a line extending between the x-ray radiator and the exposure cassette.

2. Description of the Prior Art

A slice level display of this type serves the purpose of allowing an exact acquisition and display of the height for respective tomograms, and thus allow an exact alignment to specific body slices of the patient to be acquired with the assistance of these exposures. Conventionally for this purpose the x-ray radiator and the exposure cassette are coupled by a rod (which defines the aforementioned line extending between the x-ray radiator and the exposure cassette) referred to as a slice rod, whose pivot point is height-adjustably variable on the basis of the beam from the slice level display, the slice level display being secured rigidly next to the patient support plate. Dependent on the slice level that has been set, the pivot point of the slice rod is mechanically displaced, and the horizontal plane through the swiveling axis—which also corresponds to the axis of the light ray emitted onto the patient—yields the examination slice plane in the body of the patient to be imaged.

This mechanical coupling of the x-ray radiator to the exposure cassette has the disadvantage that access by attending personnel to one of the long sides of the patient support plate is impeded, i.e. the examination can fundamentally occur proceeding only from the opposite side. In some instances, however, it would be extremely helpful if an assistant could simultaneously assist in the examination at the opposite side. Although the slice rod can be removed so that the rod itself is not disruptive given the production of actual diagnostic x-ray exposures, the rigid slice height display at the frame of the patient support plate continues to be an impediment for activities of the attending personnel at this side of the patient support table.

SUMMARY OF THE INVENTION

An object of the present invention is to provide a slice level display of the type initially described which allows the patient support plate to be completely freely accessible from all sides when no tomograms are being produced.

This object is achieved in an arrangement in accordance with the invention wherein x-ray radiator and the exposure cassette are respectively displaceable by separate drives that are each coupled to a control unit containing a position sensor which produces electronic position signals identifying the position of the light projector. The control unit uses these position signals to produce appropriate control signals for operating the respective drives of the x-ray radiator and the cassette. The projector is contained in an auxiliary unit together with a mechanism for displacement for and a height position signal generator. The auxiliary unit is detachably securable to the patient-support plate.

As a result of the inventively, electronically coupled, oppositely directed control of the x-ray radiator and of the exposure cassette, the mechanical coupling via a slice rod that was hitherto necessary is eliminated. This enables the fashioning of the projector or apparatus as a structural unit that can be detachably secured to the patient-support plate, and which is only secured to the patient-support for the production of diagnostic tomograms and can otherwise be removed with a few manipulations, so that it is not disturbing at all given utilization of the x-ray system for purposes other than tomography.

In order to be able to acquire and monitor the optical sighting ray emitted onto the patient body by the slice level display from the opposite, normal operating side in an especially simple way and in order also to be able to provide the possibility of the setting the slice level to an anomaly that has been detected (for example, swelling of the liver or the like) in the patient, in an embodiment of the invention the projector is height-adjustably arranged in a housing having a front wall, which is preferably inclined backwardly (i.e. away from the support plate), is fashioned as mirror for observing the back side of the patient with the light ray of the sighting device. The physician standing in front of the patient-support table thus can observe the patient and then set the light ray of the sighting device to the desired height position of his or her fingertips, since he or she can observe both the light ray of the sighting device and its point of incidence onto the body as well as his or her finger position in the mirror.

The front wall optionally can be fashioned as a partially reflective mirror or as a mirrored plate that has a vertical, longitudinal exit slot for the light ray. Especially advantageously, the projector contains a laser source whose beam can be spread horizontally in a plane so that it appears as a line when it strikes an opaque object, so that the exact course of the observation slice plane (important, for example, given an inclined patient-support table) can be set and monitored on the basis of a line projected onto the patient body.

In an extremely simple way, the projector can be secured to a carriage which is adjustable along a guide with a drive mechanism. The drive mechanism can, for example, contain a toothed belt drive. A height position signal is generated by a sensor in the drive motor at the carriage or the toothed belt drive, this height position signal being supplied to the control unit that controls the drives of the x-ray radiator and of the exposure cassette in a coupled manner. In this way, a coupled, oppositely directed displacement around a height-adjustable rotational axis, i.e. an axis lying in the observation slice plane, can be electronically achieved, as is produced with the significantly more complicated conventional mechanical coupling via a slice rod, that proves disturbing during operation.

For rapid mounting and unmounting of the slice level display, the housing in a further embodiment of the invention can be provided with a clamp mechanism for fastening to a lateral, profiled rail of the patient-support plate. A seating rail (flange) can be arranged at the housing above the clamp mechanism.

DESCRIPTION OF THE PREFERRED EMBODIMENTS

Figure 1:
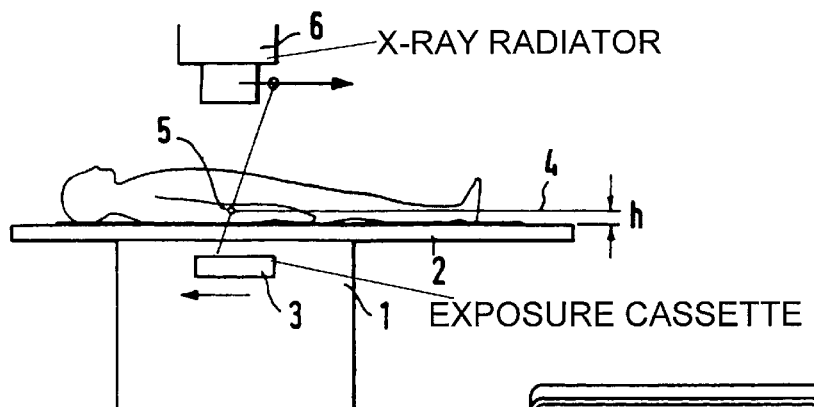
FIG. 1 is a schematic view of an x-ray system illustrating the setting and displacement of the x-ray radiator and of the exposure cassette during the production of tomograms.

In FIG. 1, one can see a patient-support plate 2 that is arranged longitudinally displaceably, and possibly tiltably as well, at a rigid carrying frame 1. The exposure cassette 3 under the patient-support plate is displaceable in a guide (not shown in detail) parallel to the longitudinal axis of the patient-support plate. The displacement ensues around a pivot point 5, lying at the set slice height 4, with the cassette 3 moving oppositely relative to the displacement direction of the x-ray radiator 6. The slice height h should be adjustable and projectable onto the body of the patient with a sighting light ray, so that the attending physician can see exactly the slice height h to which the apparatus is set.

Figure 2:
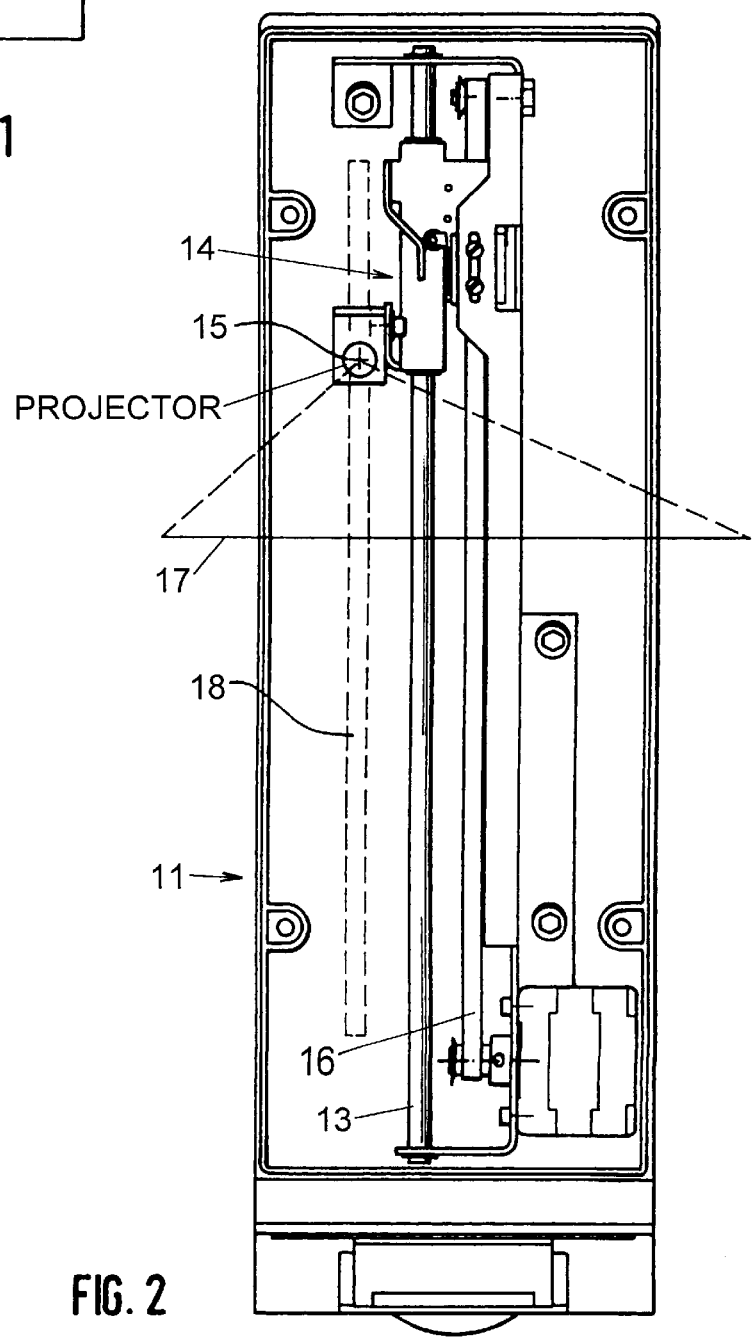
FIG. 2 is a view of an inventive slice level display with the front wall removed, which is detachably securable to the patient-support plate.
Figure 3:
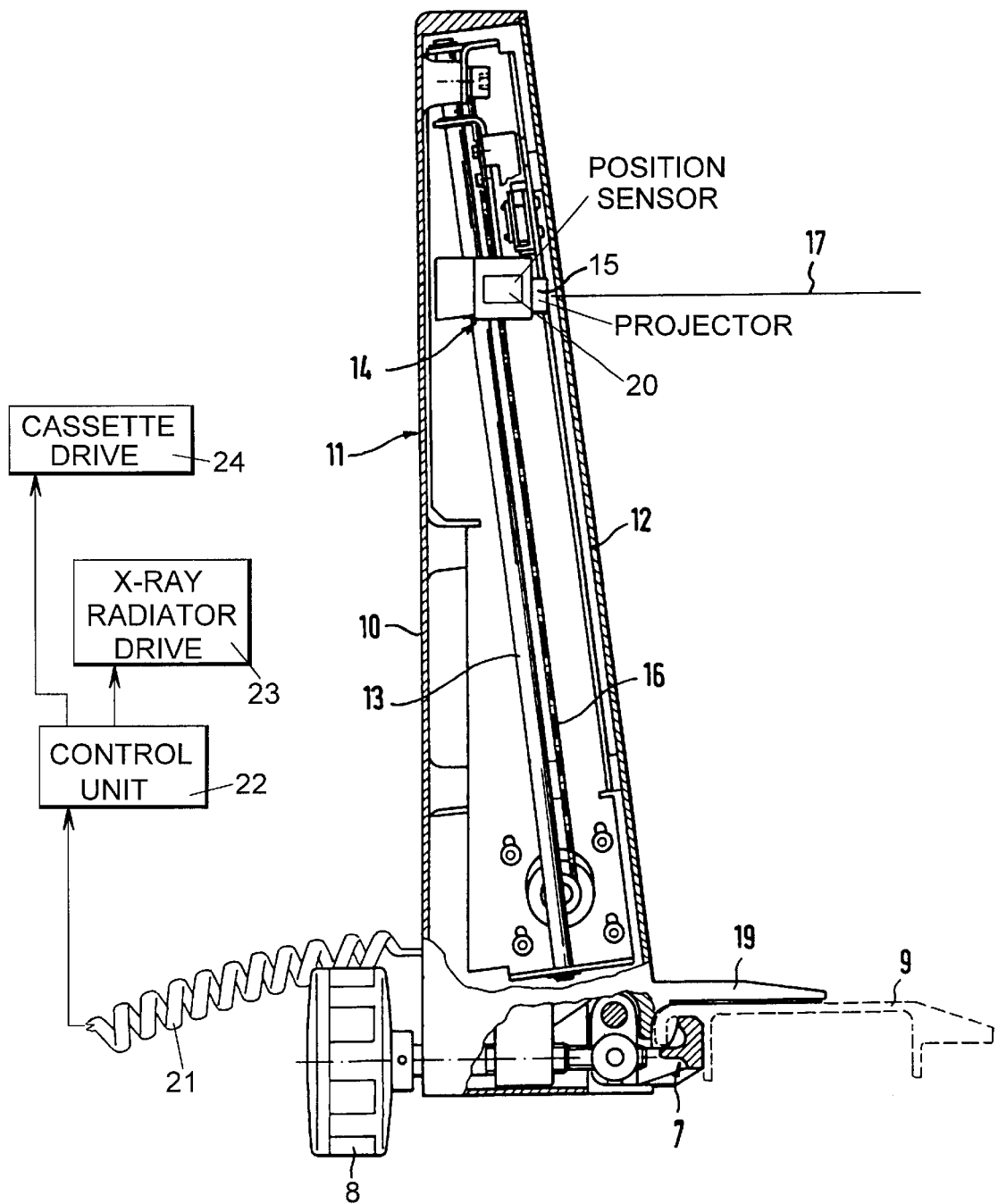
FIG. 3 is a sectional view through the slice level display of FIG. 2 taken transversely relative to the longitudinal axis of the patient-support plate.

Instead of the known, rigid mechanical coupling of the cassette 3 to the x-ray radiator 6, it is inventively provided that the exposure cassette 3 and the x-ray radiator 6 are displaceable with separate drives 23 and 24 (see FIG. 3) that are electronically coupled to one another via a control unit 22, so that oppositely directed identical displacements occur around a prescribable pivot point 5, i.e. an axis in a predetermined slice height plane 4. The corresponding height signal is supplied by a slice height display, as shown in FIGS. 2 and 3. This is an auxiliary component that can be clamped only when needed to a lateral profiled rail 9 of the patient support plate 2 (not shown in FIGS. 2 and 3) with a clamp mechanism 7 that, for example, can be actuated with a hand wheel 8. A guide 13 for a carriage 14 on which a projector 15, preferably a laser, is height-adjustably displaced is arranged in a housing 10 of the slice level display 11, the guide 13 being inclined according to the inclination of the front plate 12. The displacement ensues with a drive mechanism that contains a drive toothed belt 16. The height of the laser and of the planar light ray 17 emitted by it is acquired by a position sensor 20 and is supplied to the control unit 22 as a parameter signal from which control signals are calculated for operating the respective drive devices 23 and 24 of the exposure cassette 3 and the x-ray radiator 6.

When the projector 15 has been set by the attendant or physician to the desired height, the light ray 17 defines (i.e. is coincident with) the slice height plane 4. The control unit 22, for example, has stored therein or calculates a line (in this case an imaginary line) extending between the x-ray radiator 6 and the cassette 3, and supplies control signals to the drives 22 and 23 to cause the x-ray radiator 6 and the cassette 3 to move in opposite directions relative to a pivot point defined by the intersection of the stored/calculated line with the slice height plane 4.

The position sensor 20 is schematically shown in FIG. 3 as being located on the carriage 14 which also carries the projector 15, however, the position sensor 20 may be of any suitable type and need not be located at the carriage 14. For example, a magnetic element could be embedded in the toothed belt 16 with appropriate magnetic sensors being arranged within the housing of the slice level display 11. Another alternative is to provide a rotation counter (direction and magnitude) for one of the pulleys around which the toothed belt 16 is entrained. Moreover, although in the embodiment of FIG. 3, the position signal is supplied to the control unit 22 via a coiled cable 21 (which can also be used to contain power supply lines leading to the various components inside the slice level display 11), it is also possible for at least the position sensor 20 to be connected to a wireless transmitter in communication with a receiver at the control unit 22. Although the control unit 22 is shown in FIG. 3 as being disposed outside of the housing of the slice level display 11, the control unit 22 can alternatively be a microprocessor or a dedicated integrated circuit contained inside the housing of the slice level display 11.

The front wall 12 can be either a partially reflective mirror (externally mirrored) or, as indicated with broken lines in FIG. 2, can be provided with a longitudinal exit slot 18 for the light ray 17 and it is otherwise an opaque and externally mirrored surface. Further promoted by the slightly oblique orientation of the front plate 12, this mirrored fashioning allows proceeding from the opposite front side of the patient support plate at which the physician normally stands, the "hidden" side of the patient can be observed with the light ray 17 emitted onto the body. The position of the physician's hands can also be seen by the physician by virtue of the mirrored surface, thereby allowing the physician to identify the slice level to be x-rayed by touch. As indicated in FIG. 2, the laser contains a spreader lens arrangement, so that a "pencil" ray is not incident onto the body of the patient as a point but, instead, a sighting line is produced that enables a better adjustment of the slice plane in the body.

The inventive slice level display with the clamp mechanism 7, 8, and a seating rail or flange 19 arranged over the clamp mechanism for seating at the lateral profile rail 9 of the patient support plate, can be secured as needed to the patient support plate with practically one manipulation and can likewise be just as easily removed when not needed. No disruptive parts remain at the patient-support plate or the frame, so that the patient-support table is freely accessible from all sides when not being employed for tomograms.

The invention is not limited to the illustrated exemplary embodiment. Of course, the light projector 15 need not be a laser and the type of height adjustment of the light projector can also ensue in some other way. Important features of the present invention are offering a height position signal with a removable slice level display and the oppositely directed control of the x-ray radiator and the exposure cassette by separate drives, with a control unit coupling them and in which the slice level signal is also processed.

Although various minor modifications might be suggested by those skilled in the art, it should be understood that our wish to embody within the scope of the patent warranted hereon all such modifications as reasonably and properly come with the scope of our contribution to the art.

We claim as our invention:

1. A slice level display for an x-ray system having a patient support plate and an x-ray radiator and an exposure cassette disposed on opposite sides of said patient support plate, said patient support plate being adapted to receive a patient thereon, said slice level display comprising:

a first drive for displacing said x-ray radiator;

a second drive, separate from said first drive, for displacing said exposure cassette;

a projector which emits a planar light beam;

positioning means for selectively positioning said projector and said light beam at a selected height above said support plate;

position sensor means for generating a position signal identifying a height of said projector and light beam;

control means for operating said first drive and said second drive for displacing said exposure cassette and said x-ray radiator in respectively opposite directions around a pivot point defined by an intersection of said light beam and a line extending between said x-ray radiator and said exposure cassette; and a housing containing at least said projector, said position sensor means and said positioning means, and means for detachably connecting said housing to said patient support plate.

2. A slice level display as claimed in claim 1 wherein said housing has a front wall having an exterior mirrored surface facing toward said patient support plate.

3. A slice level display as claimed in claim 2 wherein said front wall is inclined at an angle larger than 90° relative to said patient support plate.

4. A slice level display as claimed in claim 2 wherein said front wall is a semi-reflective mirror so that said light beam passes therethrough.

5. A slice level display as claimed in claim 2 wherein said front wall comprises a vertical, longitudinal exit slot through which said light beam passes.

6. A slice level display as claimed in claim 1 wherein said projector comprises a laser which emits a laser beam and including means for horizontally spreading said laser beam to form said planar light beam.

7. A slice level display as claimed in claim 1 wherein said positioning means comprises a carriage, to which said projector is attached, and a guide along which said carriage is moveable in said housing, and drive means for displacing said carriage along said guide.

8. A slice level display as claimed in claim 7 wherein said drive means comprises a toothed belt entrained around rotatable wheels.

9. A slice level display as claimed in claim 1 wherein said patient support plate has a lateral profiled rail, and wherein said means for detachably attaching said housing to said patient support plate comprises a clamp mechanism for releasably fastening said housing to said lateral profile rail.

10. A slice level display as claimed in claim 9 wherein said housing comprises a seating rail projecting from said housing above said clamp mechanism and extending over said patient support plate.

\* \* \* \* \*